United States Patent [19]

Dennis

[11] Patent Number: 4,630,613

[45] Date of Patent: Dec. 23, 1986

[54] PULSE DETECTION

[75] Inventor: Christopher J. Dennis, Harrogate, England

[73] Assignee: Equipaid Limited, West Yorkshire, England

[21] Appl. No.: 508,278

[22] Filed: Jun. 27, 1983

[30] Foreign Application Priority Data

Jun. 26, 1982 [GB] United Kingdom ............... 8218563

[51] Int. Cl.⁴ ................................................ A61B 5/02
[52] U.S. Cl. ................................... 128/687; 128/775; 128/903
[58] Field of Search .................... 128/687-690, 128/736, 903, 738, 775

[56] References Cited

U.S. PATENT DOCUMENTS

| | | | |
|---|---|---|---|
| 2,583,941 | 1/1952 | Gordon, Jr. ................... | 128/687 X |
| 3,082,414 | 3/1963 | Papaminas .......................... | 128/687 |
| 3,442,263 | 5/1969 | Pascaud ............................... | 128/690 |
| 3,742,937 | 7/1973 | Manuel et al. ...................... | 128/690 |
| 3,811,429 | 5/1974 | Fletcher et al. .................... | 128/687 |
| 3,851,320 | 11/1974 | Dahl .................................. | 128/689 X |
| 3,972,320 | 8/1976 | Kalman .......................... | 128/690 X |
| 4,090,504 | 5/1978 | Nathan ............................. | 128/689 X |
| 4,100,536 | 7/1978 | Ball et al. ........................ | 128/689 X |
| 4,232,686 | 11/1980 | Kammlade, Jr. ................... | 128/775 |
| 4,252,128 | 2/1981 | Kane .................................. | 128/690 |
| 4,411,274 | 10/1983 | Wright ............................. | 128/775 X |

Primary Examiner—Kyle L. Howell
Assistant Examiner—Angela D. Sykes
Attorney, Agent, or Firm—Brooks & Kushman

[57] ABSTRACT

This invention relates to apparatus for monitoring the pulse rate of a human or animal subject, including a pulse detector for attachment to the subject which produces a pulse signal corresponding to the pulse of the subject, a transmitter which transmits the pulse signal to a remote signal analyzer and indicator which exhibits a characteristic of the pulse. The indicator may be a monitor to continuously display the pulse rate or an alarm which indicates an increase in pulse rate. The invention also provides a method of detecting pain by detecting an increase in pulse rate using the apparatus. The invention also relates to a new pulse detection method for an animal for attachment to the underside of the tail of the animal.

3 Claims, 6 Drawing Figures

PULSE DETECTION

This invention relates to improvements in detection of pulse rate of a human or animal subject and in particular to an apparatus for detecting pulse rate and to a method of detecting pain, especially labour pain in a pregnant animal, by detecting an increase in pulse rate.

It is common practice to keep animals, especially horses, under constant and direct human supervision during the last stages of pregnancy in order to ensure that assistance is provided during delivery. This is inconvenient and expensive but has been necessary because no sufficiently effective reliable and economic automatic warning system has been available.

According to one aspect of this invention there is provided apparatus for monitoring the pulse rate of a subject, including animal and human subjects, comprising pulse detection means for attachment to the subject body which, in use produces a pulse signal corresponding to the pulse of said subject, transmitter means coupled to said pulse detection means for transmitting the pulse signals to a remote signal analyser, pulse indicator means coupled to said signal analyser and responsive to analysed signals therefrom to exhibit at least one characteristic of the pulse of the subject.

The pulse indicator means may either visually display the pulse rate or may provide an alarm when the pulse rate has increased. Preferably an alarm is only given when a pulse rate has been at an increased rate for a predetermined time.

According to a further aspect of the present invention there is provided a method of detecting pain in a subject comprising detecting the pulse of said subject and producing a pulse signal corresponding to said pulse, transmitting said pulse signal to a remote signal analyser, and producing an alarm actuating signal in response to an increase in the rate of pulse, to actuate an alarm to signal pain in the subject.

Preferably the transmitter means used in the apparatus and the method comprises a UHF transmitter attachable to the animal, an appropriate receiver being connected to said signal analyser close to but out of contact range with the animal so that movement of the animal is unimpeded. This means that a signal is conveyed which varies steadily with the skin movement associated with the pulse beat but conveys signals which are independent of any movement of the animal.

According to a further aspect of this invention there is provided apparatus for detecting the pulse of an animal for placing on the underside of the tail of the animal.

It has been found that a pulse is detectable tied near the stub of the tail of the animal. This position is suitable since the tail protects the detector. Preferably the detector comprises a closed hollow structure including a flexible surface for placing against the root of the tail of the animal, fluid substantially filling said structure and means to detect movement of said fluid, said movement detection means producing a signal responsive to said movement whereby movement of said tail caused by a pulse in said animal causes said flexible surface to move whereby said fluid moves and said fluid movement detection means produces a pulse signal. The flexible structure is held in close contact with the skin at the root of the tail and moves with the pulse beat in the skin. Relative movement of the flexible surface can be detected in any convenient way for instance by changes in internal pressure or volume or electrical capacity.

Preferably the movement of the fluid is detected by a magnetic flux detector.

It is preferable that the apparatus also includes a temperature sensor for attachment to said subject. Preferably the sensor is included in the pulse detection means and is coupled to said transmitter means, the transmitter means also transmitting temperature signals to the signal analyser the apparatus also including temperature indicator means coupled to the signal analyser and responsive to analyse signals therefrom to exhibit at least one characteristic of the temperature of the subject.

Preferably the temperature indicator means is an alarm means responsive to a signal from the analyser produced on an increase in temperature to produce an alarm.

The apparatus is particularly valuable in warning of the onset of delivery of an animal because non-periodic signals due to other causes and short-lived changes in pulse rate due to transient high pain levels can both be ignored since the alarm may be actuated only by a long period of consistently high pulse rate due to a long period of consistently high pain.

A method and apparatus in accordance with the invention will now be described, by way of example only, with respect to the following drawings, in which.

Figure 1:
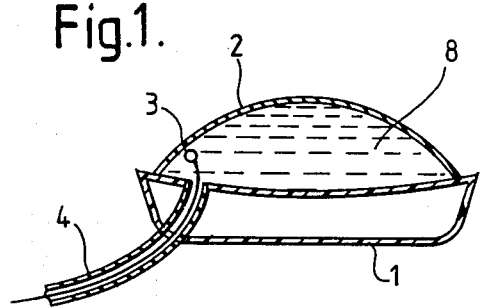
FIG. 1 is a schematic section through a pulse detector in accordance with the invention.
Figure 2:
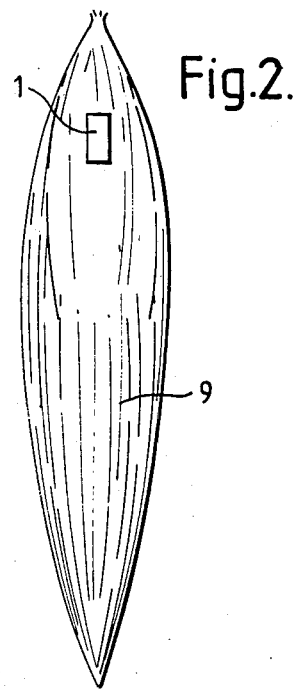
FIG. 2 shows the position of the pulse detector on the underside of the tail of a horse.
Figure 3:
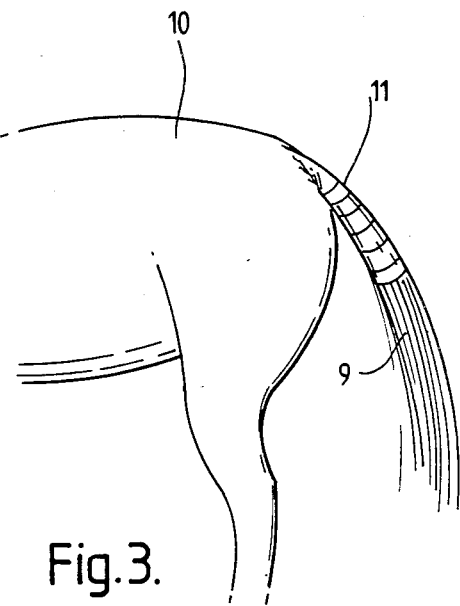
FIG. 3 is a schematic perspective view of the positioning of the pulse detector on the horse.
Figure 4:
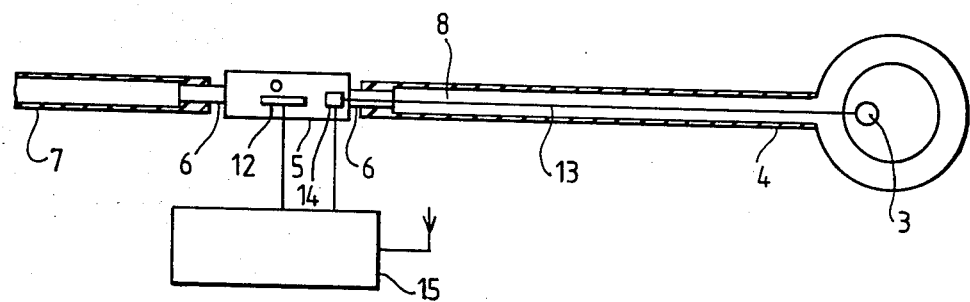
FIG. 4 is a longitudinal section of apparatus in accordance with the invention.

The example of the apparatus described is for the detection of pulse rate of a horse.

A pulse rate detector comprises a dish-shaped rigid plastic member 1 of GRP and a semi-spherical rubber diaphragm 2. Located within rubber diaphragm 2 is a bead thermistor 3.

Rigid dish-shaped member 1 and diaphragm 2 define a space from which extends a rubber sleeve 4 which extends along a flexible tube, 6 a detector unit 5 and a further tube 7. This space is totally enclosed and contains fluid 8. Movement of the rubber diaphragm 2 causes fluid 8 to move. The detector is placed on the underside of the tail 9 of a horse 10 near the root of the tail where a pulse is detectable. The flexible diaphragm is placed nearest the skin of the tail with the rigid plastics member 1 outermost.

The detector is fastened to the tail 9 by standard tail bandaging 11 which holds the detector firmly to the tail and protects it from movement of the animal.

Within detector unit 5 is a mechanical flux detector 12 which detects any movement of the fluid 8 within the enclosed space. From bead thermistor 3 extend wires 13 to a temperature detector 14 in the detector unit 5. Detector unit 5 is coupled to a data unit and UHF transmitter 15. UHF transmitter 15 transmits a signal consisting of a carrier with a variation in one modulation aspect indicative of the pulse rate and a secondary signal including continual data on the temperature of the animal.

Figure 5A:
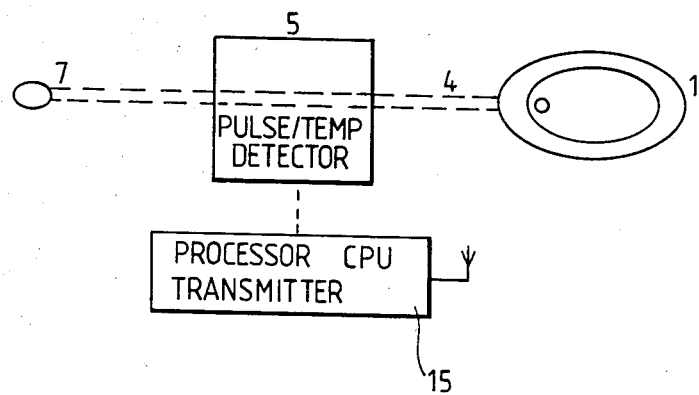
FIG. 5 is a schematic block diagram of the transmitter means and signal analyser means of the apparatus.
Figure 5B:
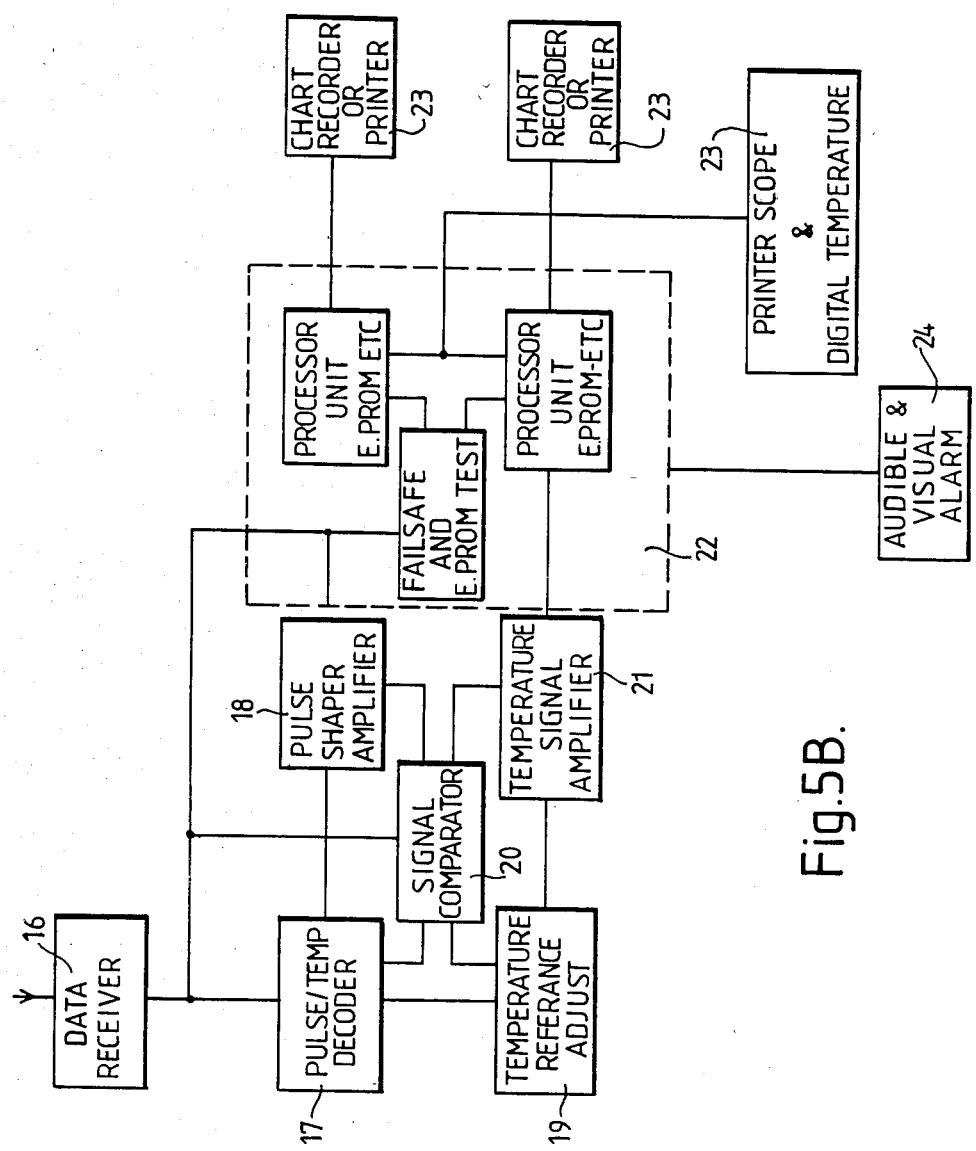

The UHF signals are transmitted to a remote signal analyser shown in FIG. 5B including a UHF receiver 16 which feeds signals to a decoder 17 which feeds a pulse signal to a pulse shaper amplifier 18 and a temperature signal to a temperature reference adjust 19. These signals are then fed to a signal comparator 20 which compares the pulse and temperature signals with reference signals held in the signal comparator 20. The temperature reference signal is then fed from the temperature reference adjust to an amplifier 21 via a processor unit shown generally at 22. From processor unit 22 is fed signals to a chart recorder or printer 23. This provides a continuous read-out of the temperature of the animal.

The pulse signals are fed from a pulse shaper amplifier 18 to the signal comparator 20 where the signals are compared with pulse signals already held in the comparator. These signals are then fed from the comparator to the processor unit 22 which provides a read-out to the chart recorder and printer 23 to provide a continuous read-out of the pulse rate and also provides an output to alarm means 24 to provide an alarm when the pulse rate has increased for a predetermined time.

The processor unit 22 includes means to monitor the depth of pulse by comparing consecutive pulse signals in the comparator 20 to check that the pulse is strong enough.

This apparatus may be used to provide an alarm when the pulse rate of the horse has been increased for a predetermined time for instance when the animal is in labour.

I claim:

1. A method for monitoring the pulse rate of an animal having a tail with a root attached to the body of the animal, the methd comprising: detecting the pulse at the root of the tail of said animal, producing a pulse signal corresponding to said pulse of said animal, transmitting said pulse signal to a remote signal analyzer which includes a pulse indicator means which is responsive to analyzed signals, and exhibiting on the indicator means at least one characteristic of the pulse of the animal.

2. A method according to claim 1 wherein pain in the animal is detected, the pulse indicator means being responsive to an increase in pulse rate sufficient to indicate that the animal is in pain.

3. A method according to claim 2 wherein the onset of labor pain in a pregnant animal is detected.

* * * * *